United States Patent [19]
McCall et al.

[11] Patent Number: 5,921,239
[45] Date of Patent: Jul. 13, 1999

[54] FACE MASK FOR PATIENT BREATHING

[75] Inventors: Shawn R. McCall, Somerset; Daniel E. Kimble, Rockwood; Allan R. Jones, Jr., Derry, all of Pa.

[73] Assignee: Sunrise Medical HHG Inc., Longmont, Colo.

[21] Appl. No.: 08/779,395

[22] Filed: Jan. 7, 1997

[51] Int. Cl.⁶ .................................................. A62B 18/02
[52] U.S. Cl. .............................. 128/205.25; 128/206.24; 128/206.26; 128/207.11
[58] Field of Search ..................... 128/202.27, 205.25, 128/911, 912, 206.24, 206.26, 207.11

[56] References Cited

U.S. PATENT DOCUMENTS

| | | | |
|---|---|---|---|
| 2,473,518 | 6/1949 | Garrard et al. | 128/205.25 |
| 3,330,273 | 7/1967 | Bennett | 128/206.24 |
| 3,978,854 | 9/1976 | Mills, Jr. | 128/912 |
| 4,233,972 | 11/1980 | Hauff et al. | 128/205.12 |
| 4,454,881 | 6/1984 | Huber et al. | 128/206.15 |
| 4,676,241 | 6/1987 | Webb et al. | 128/912 |
| 4,686,977 | 8/1987 | Cosma | 128/912 |
| 4,807,617 | 2/1989 | Nesti | 128/205.25 |
| 4,905,683 | 3/1990 | Cronjaeger | 128/202.22 |
| 5,074,297 | 12/1991 | Venegas | 128/205.25 |
| 5,243,971 | 9/1993 | Sullivan et al. | 128/205.25 |
| 5,301,689 | 4/1994 | Wennerholm | 128/205.25 |
| 5,419,318 | 5/1995 | Tayebi | 128/205.27 |
| 5,538,001 | 7/1996 | Bridges | 128/206.24 |
| 5,540,223 | 7/1996 | Starr et al. | 128/205.25 |
| 5,542,128 | 8/1996 | Lomas | 128/207.11 |
| 5,560,354 | 10/1996 | Berthon-Jones et al. | 128/205.25 |
| 5,570,689 | 11/1996 | Starr et al. | 128/207.11 |
| 5,662,101 | 9/1997 | Ogden et al. | 128/205.25 |
| 5,709,204 | 1/1998 | Lester | 128/205.25 |

FOREIGN PATENT DOCUMENTS

3707952 A1  3/1987  Germany.

*Primary Examiner*—Aaron J. Lewis
*Attorney, Agent, or Firm*—MacMillan, Sobanski & Todd, LLC

[57] ABSTRACT

A mask for directing air to the facial area of a patient includes a mask body in the form of a conduit, a seal connected to an outlet end of the mask body for contacting the patient's face in a sealing relationship, the seal being soft and pliable for patient comfort, and a vent tube connected to an inlet end of the mask body to supply air to the mask body. The mask body is relatively flexible compared with the vent tube so that lateral stresses on the mask body are initially accommodated by distortion of the mask body rather than on breaking the sealing relationship between the seal and the patient's face. A frame is mounted for movement along the mask body to press the seal against the patient's face. The frame includes a nose bridge portion, an upper jaw portion, and two lateral portions, and the two lateral portions of the frame are contoured to conform to the shape of the seal so that gentle contact between the frame and the seal causes only the two lateral portions of the frame to touch the seal. A spacer is positioned between the frame and the seal, where the spacer is adjustable to vary the contact between the frame and the seal, thereby enabling the frame to selectively press against the seal so that the shape of the seal can be modified to conform to the shape of the patient's face. The vent tube can be connected to the mask body with a ball and socket connection and an exit air vent which directs exhaled air away from the patient's face.

31 Claims, 4 Drawing Sheets

FACE MASK FOR PATIENT BREATHING

TECHNICAL FIELD

This invention relates to respiratory masks suitable for being applied to a patient's face to supply air or oxygen to the patient for breathing. More particularly, this invention provides a respiratory mask that is comfortable for patients to use, and that enables the patient to move around somewhat relative to the supply of air without breaking the seal between the mask and the patient's face.

BACKGROUND OF THE INVENTION

Face masks have long been used to administer air, oxygen or other gases to patients for various purposes, such as administering anesthesia, providing oxygen delivery for critical patients, and counteracting sleep apnea. The face masks are connected with tubes or hoses to a pressurized source of air or other breathing gases. A vent tube is usually provided to connect the face mask with the hose to supply the air to the mask. The face masks have a seal roughly contoured to match a typical human face. The mask is usually held in place against the patient's face by headgear including adjustable straps that extend around the patient's head and force the mask into a sealing engagement with the patient's face.

One of the problems with current breathing face masks is that under certain conditions it is difficult to maintain the seal between the mask and the patient's face, particularly when the patient is moving his head. Normal sleep patterns usually include some head movement, whereas the air supply hose extends from the air source at a fixed location. The lateral stress applied to the mask caused by relative movement between the patient's head and the air supply hose can easily break the seal to the patient's face, thereby defeating the goal of supplying the air or other breathing gases into the patient's respiratory system.

Efforts to provide the masks with a more reliable connection seal to the patient's face have resulted in the development of a swivel connection to prevent twisting of the air hose. Another advance in masks is to use a short vent tube having a right angle bend to minimize lateral stresses on the mask generated by movement of the patient's head relative to the air hose. The short vent tube has a reduced moment arm of bending when compared with vent tubes extending straight away from the face. Angled vent tubes are shown in U.S. Pat. No. 5,492,116 to Scarberry at al., for example. In spite of these improvements, however, there is still a great need for respiratory masks enabling more secure connections with the patient's face to prevent the loss of the seal.

Another problem with current breathing face masks is that they are uncomfortable to wear. To maintain a good seal the mask must be pressed against the patient's face. If the pressure of the mask against the patient's face is too great, the patients will be reluctant to use the mask. To counteract this deficiency, respiratory masks have been provided with seals of flexible, resilient material to soften and distribute the pressure of the mask against the face. While this has made the masks more comfortable, further improvements in comfort are needed.

Another aspect of respiratory masks is that means must be provided for adequate venting of the air exhaled by the patient. Without some type of venting, the exhaled air will merely accumulate in the mask or in the vent tube, with a resulting increase in the carbon dioxide level of the air supplied to the patient. Consequently, exit air ports for exhaled air are provided in most respiratory masks. For example, apertures in the mask body for the exhaled air of the patient are shown in U.S. Pat. No. 4,328,797. A problem with these exit air ports is that the rush of exhaled air generates noise and an air pulse which can disturb the patient or the patient's sleeping partner. An improved respiratory mask would provide for a quieter and less forceful exit of exhaled air.

SUMMARY OF THE INVENTION

The above objects as well as other objects not specifically enumerated are achieved by a mask for directing air to the facial area of a patient which includes a mask body in the form of a conduit, a seal connected to an outlet end of the mask body for contacting the patient's face in a sealing relationship, the seal being soft and pliable for patient comfort, and a vent tube connected to an inlet end of the mask body to supply air to the mask body. The mask body is relatively flexible compared with the vent tube so that lateral stresses on the mask body are initially accommodated by distortion of the mask body rather than on breaking the sealing relationship between the seal and the patient's face.

In another embodiment of the invention, a frame is mounted for movement along the mask body to press the seal against the patient's face.

In another embodiment of the invention, the frame includes a nose bridge portion, an upper jaw portion, and two lateral portions, and the two lateral portions of the frame are contoured to conform to the shape of the seal so that gentle contact between the frame and the seal causes only the two lateral portions of the frame, to touch the seal.

In yet another embodiment of the invention, a spacer is positioned between the frame and the seal, where the spacer is adjustable to vary the contact between the frame and the seal, thereby enabling the frame to selectively press against the seal so that the shape of the seal can be modified to conform to the shape of the patient's face.

In still another embodiment of the invention, the vent tube is connected to the mask body with a ball and socket connection and an exit air vent which directs exhaled air away from the patient's face.

DETAILED DESCRIPTION AND PREFERRED EMBODIMENTS OF THE INVENTION

Figure 1:
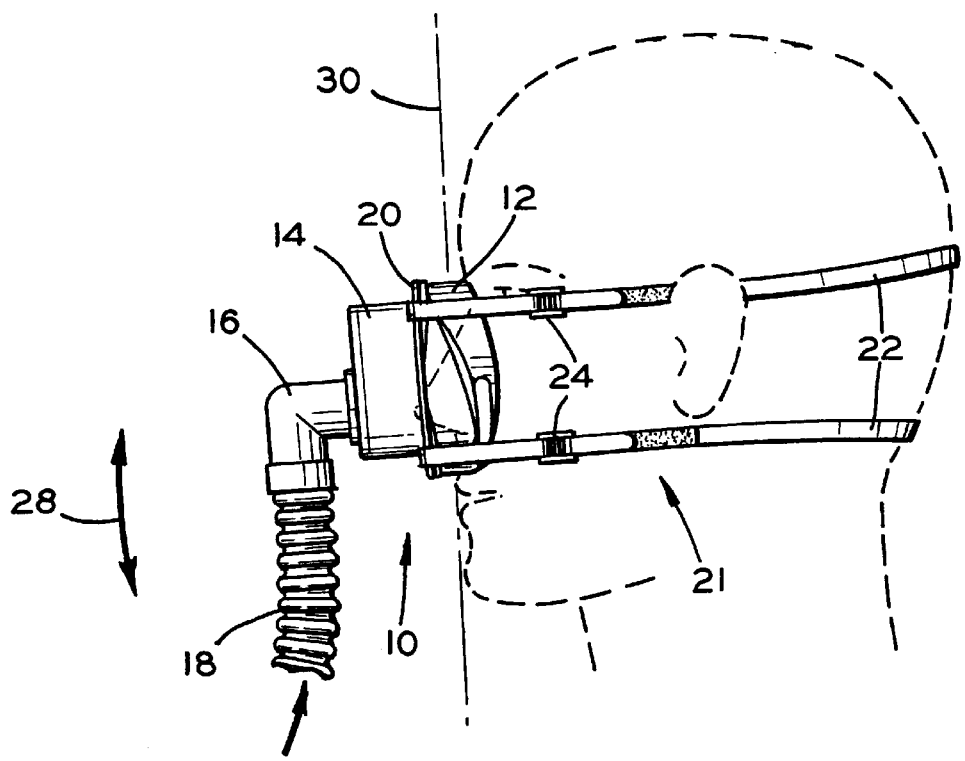
FIG. 1 is a schematic view in elevation of the respiratory mask of the invention.
Figure 3:
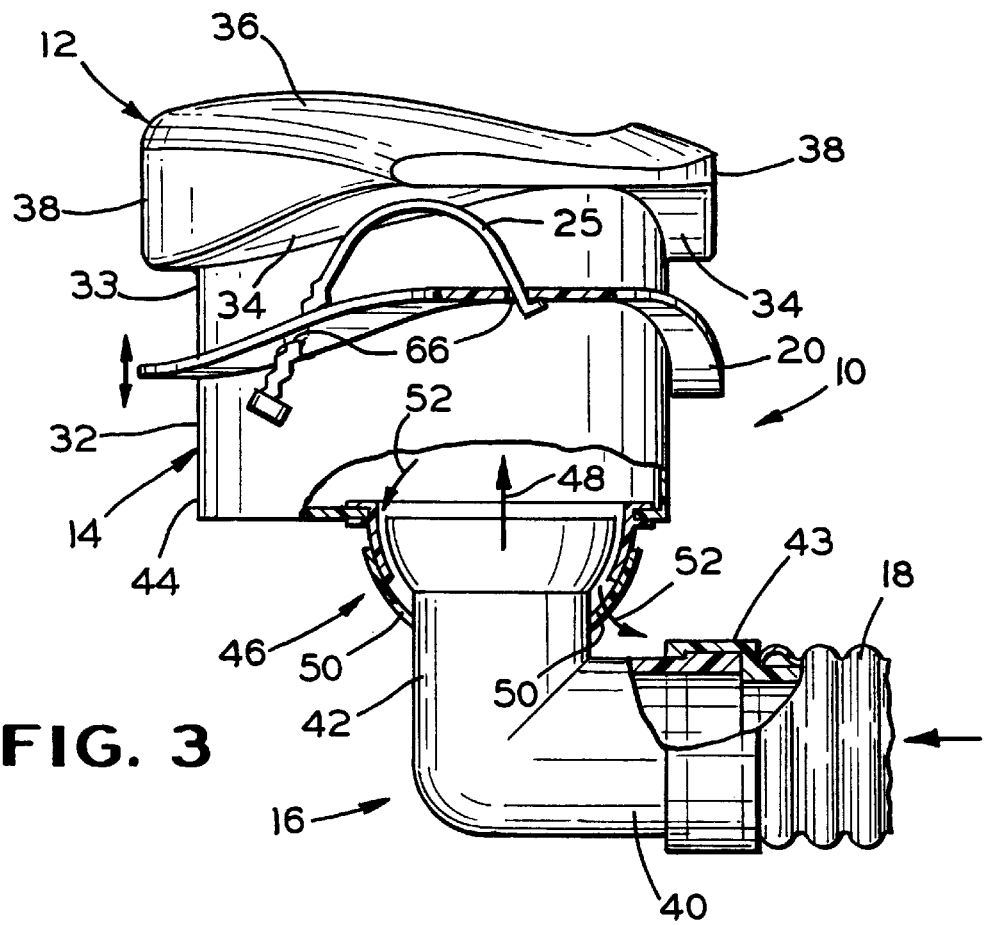
FIG. 3 is a schematic plan view, partially in cross-section, of the mask of the invention.

As shown in FIGS. 1 and 3, the mask, indicated generally at 10, is comprised of a seal 12, a mask body 14 and a vent tube 16. The vent tube is supplied with air or other breathable gases from a source, not shown, via air supply hose 18. The frame 20 is mounted for slidable movement along the mask body 14 to urge the seal 12 against the face of the patient. Headgear 21, including straps 22 with Velcro adjustments 24, can be used to pull the frame 20 toward the face of the user. A spacer 25 is positioned between the frame and the seal to enable the frame to selectively press against the seal so that the shape of the seal can be modified to conform to the shape of the patient's face. The spacer allows the contact between the frame and the seal to be varied.

Figure 4:
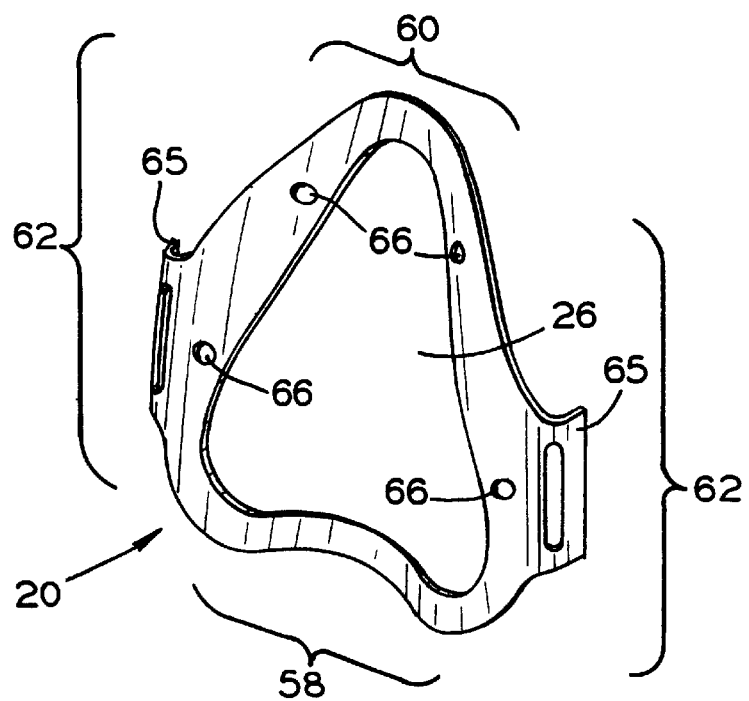
FIG. 4 is a schematic view in perspective of the frame shown on the mask of FIGS. 1 and 3.

The frame 20 has a central opening 26, shown in FIG. 4, which enables the frame to be moved or slid along the mask body. Since the frame opening 26 is larger than the cross-sectional size of the mask body, the mask body can rotate relative to the frame, as indicated by arrow 28. Both the mask body 14 and the frame 20 can rotate relative to the plane 30 of the patient's face. This feature of the invention allowing the frame to be angled with respect to the mask body enables the mask body to move somewhat independently of the frame.

Figure 2:
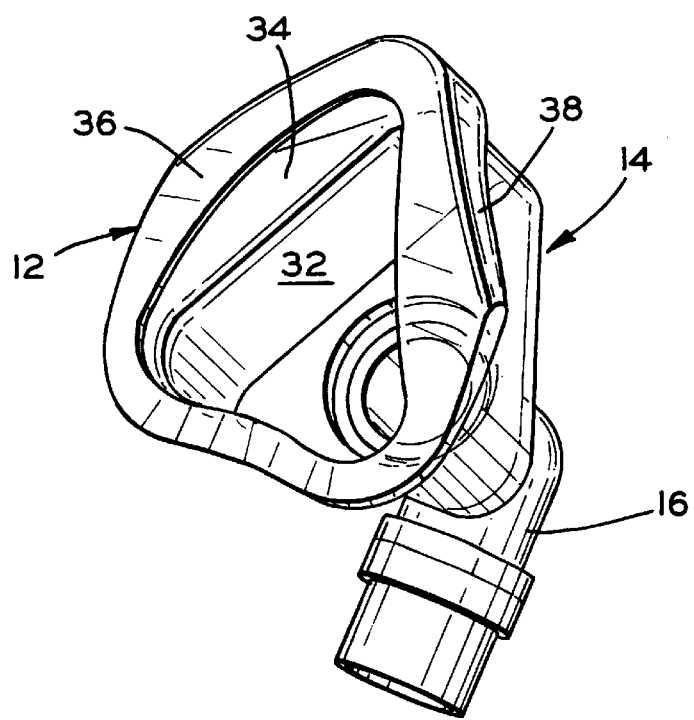
FIG. 2 is a schematic view in perspective of the mask body and seal of the mask of the invention.

As shown in FIGS. 2 and 3, the mask body 14 is in the form of a conduit for supplying air to the patient. The mask body has sidewalls 32, and the seal 12 is connected to the mask body at the mask body outlet end 33. The seal 12 has a mask body flange 34 and a patient face flange 36 which are connected to each other by a circumferential edge 38 in the form of a fold or joint. The hinging or folding of the mask body flange and a patient face flange gives a spring-like resiliency to the seal 12.

The vent tube 16 can be any design suitable for supplying air to the mask body. Preferably it is made of a hard or rigid plastic material, such as a translucent polyethylene. The preferred vent tube has a right angle bend dividing the vent tube into a supply leg 40 and a body leg 42. The vent tube can be connected to the air supply hose 18 by any suitable joint, such as by a swivel connection 43, as shown in FIG. 3.

The vent tube is connected to the inlet end 44 of the mask body with a joint. Although several types of joint can be used, a ball and socket connection 46 is preferred. The ball and socket joint allows fresh air to be delivered from the vent tube 16 into the mask body 14, as indicated by directional arrow 48. Exhaled air leaves the mask body through the exit air vents 50 via a different exit air path, as indicated by exit air path arrows 52. The ball and socket joint enables the vent tube to be angled or rotated with respect to the mask body, thereby enabling a greater amount of freedom of movement without dislodging or breaking the sealing relationship between the seal 12 and the patient's face. A sealing relationship is established when the seal 12 is pressed against the patient's face with enough force to close off any external air path to the patient's nose so that substantially all of the air breathed in and exhaled by the patient will pass through the mask body. It can be appreciated that if the seal 12 is moved so that the seal no longer closes off the alternate paths to the patient's nose, the sealing relationship will be broken and outside air can be breathed in and exhaled by the patient along paths other than the paths indicated by arrows 48 and 52. An example of movement of the mask 10 to break the seal would be excessive rotation of the mask body 14 in the direction indicated by arrow 28.

Figure 8:
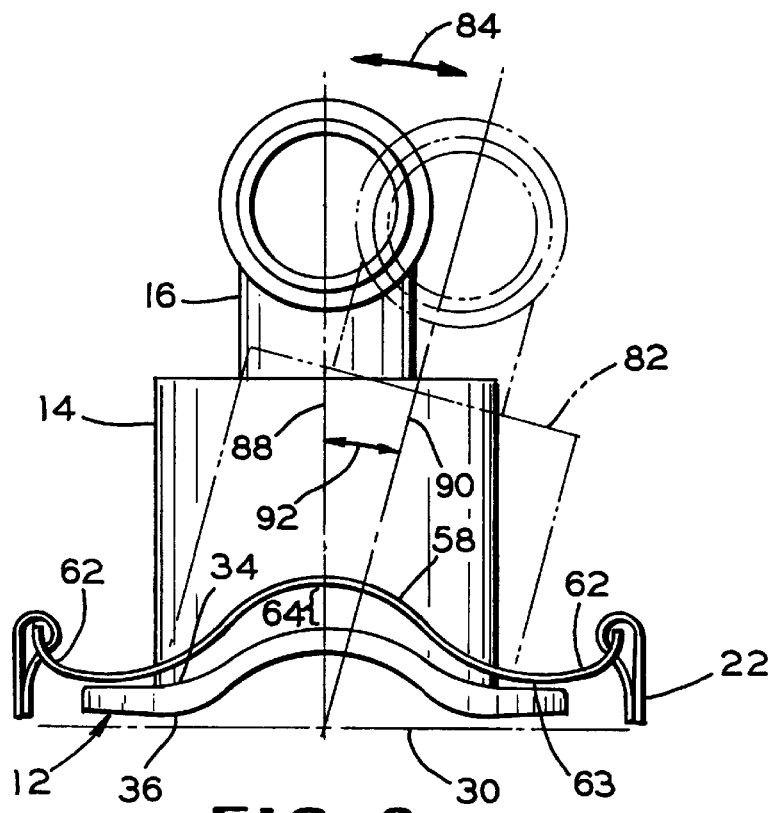
FIG. 8 is a schematic plan view of the mask of the invention illustrating lateral movement of the vent tube without moving the seal.

As shown in FIG. 4, the frame 20 is a generally planar element with central opening 26. The frame can be divided into an upper jaw portion 58, a nose bridge portion 60 and two lateral portions 62. The frame is contoured so that when pressed against the seal it applies different forces or pressures to different areas of the seal, and therefore applies different pressure to different areas of the patient's face. In a preferred design of the seal and frame, the two lateral portions of the frame are contoured to conform to the shape of the seal so that gentle contact between the frame and the seal causes the two lateral portions of the frame to touch the seal, and the nose bridge and upper jaw portions of the frame are contoured out of conformance with the shape of the seal so that gentle contact between the frame and the seal does not cause the nose bridge and upper jaw portions of the frame to touch the seal. This means that the initial contact between the frame and the seal will be in the two lateral portions of the frame. This can be seen in FIG. 8, where the lateral portions 62 are practically in contact (indicated at 63) with the mask body flange 34 of the seal, whereas the upper jaw portion 58 is still separated from, and out of conformance with, the body flange 34 of the seal. As shown in FIG. 8, the upper jaw portion 58 is separated from the seal by a substantial distance or gap 64. Preferably, a similar gap, not shown, is formed in the nose bridge area 60 of the frame. The added clearance in the upper jaw portion 58 and the nose bridge area allows the flexible seal 12 to conform to the patient's face without creating pressure points on the face.

As shown in FIG. 4, the frame has a pair of lugs 65 for attachment of the straps 22 of the headgear 21. The pulling force of the straps on the lugs forces the frame to slide along the mask body as far as possible toward and in contact with the seal, thereby forcing the mask against the patient's face. The Velcro adjustments 24, shown in FIG. 1, control the overall force applied to the seal by the frame.

Figure 5:
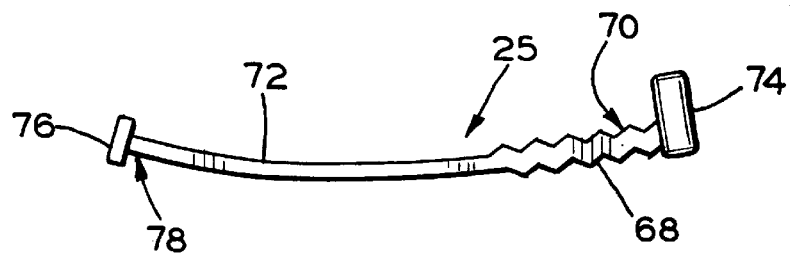
FIG. 5 is a schematic view in elevation of the spacer shown in FIG. 3.

The frame is provided with spacer orifices 66 through which the spacer 25 is extended. The spacer, as shown in FIG. 5 is a bendable elongated member, and has a ratchet 68 at the ratchet end 70. The ratchet includes a series of projections or ridges and notches which enable the ratchet end 70 of the spacer to be adjustably fixed at a desired location within the spacer orifice 66. The remainder of the spacer 25, referred to as the central portion 72, does not have the ratchet 68, but is smooth for easier sliding through its associated spacer orifice. The spacer is provided with stop end 74 at the ratchet end 70, and stop end 76 at the distal end 78, to secure the spacer within the spacer orifices so that the spacer cannot slide completely out of the spacer orifices. The spacer is preferably constructed with the ratchet end 70 of the spacer being relatively stiff compared to the central portion 72 of the spacer. In operation, the spacer can be adjusted by fixing the ratchet at a desired position through the spacer orifice. As shown in FIG. 1, the central portion 72 of the spacer is more flexible and is bowed out toward the seal, with the distal end 78 of the spacer extending through its corresponding spacer orifice 66.

The use of the spacer enables the patient to adjust the mask of the invention so that maximum comfort can be obtained. The spacer controls the relative amount of force applied to various areas of the seal by the frame. Since the spacer is mounted in the lateral portions 62 of the frame, the spacer allows adjustment of the force applied to the soft facial areas along the sides of the patient's nose. Increased extension of the ratchet end 70 of the spacer toward the seal will result in a greater pressing of the seal in those areas, and a consequent backing off or reduction in pressure on the nose bridge and the upper jaw of the patient.

Figure 6:
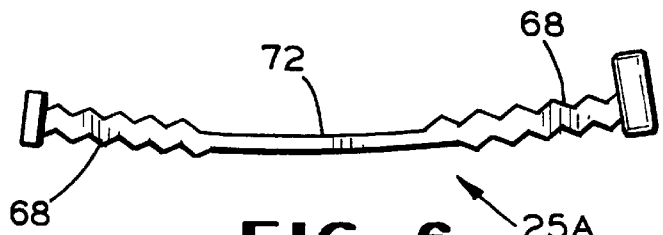
FIG. 6 is a schematic view in elevation of a different spacer.

As shown in FIG. 6, in an alternate embodiment of the spacer of the invention, the spacer 25A has a ratchet 68 at both ends. Central portion 72 is more flexible than the ratchet and will bow or bend to enable the two ratchets to be inserted into the spacer orifices.

Figure 7:
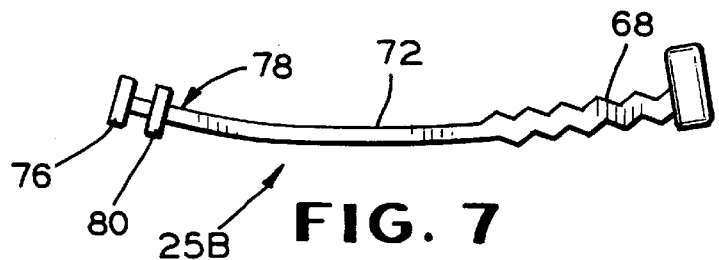
FIG. 7 is a schematic view in elevation of yet another spacer.

As shown in FIG. 7, in another alternate embodiment of the spacer of the invention, the spacer 25B has an additional stop end 80 which combines with stop end 76 to fix the distal end 78 of the spacer with respect to the frame. The ratchet end 70 is still adjustable.

The mask body 14 and the seal 12 are preferably both made of flexible, resilient material. The flexibility of the material for both the seal and the mask body increases the comfort to the patient and increases the likelihood that the mask will stay in place and in a sealing relationship even when the vent tube is moved. The mask body and the seal can be made of any flexible material, examples of which include synthetic rubber, such as Kraton® rubber, and vinyl materials. A preferred material is a silicone material. The softness of the material can be measured with a durometer, which is used to measure soft, elastic materials, such as rubbers and non-rigid plastics. The durometer measures the resistance of the material to elastic penetration. A preferred durometer Shore-A level for the material used in the mask body and the seal is within the range of from about 30 to about 60, with a most preferred level at about 40. The thickness of the mask body sidewall 32 also affects the ability of the mask body to deform without breaking the sealing relationship between the seal and the patient's face. Also, the thickness must be sufficient to ensure that the mask body can support the vent tube without collapsing. Preferably, the thickness of the sidewall is within the range of from about 0.045 to about 0.090 inch (1.01 to 2.02 mm), although other thicknesses can be used. A preferred thickness is about 0.062 inch (1.57 mm). The seal and the mask body need not be made of the same material, but a preferred method of making the seal and the mask body is to mold them integrally together into a single entity using compression molding.

As shown in FIG. 8, the mask body 14 is flexible enough so that the vent tube 16 and a portion of the mask body 14 can be moved laterally, as indicated by the phantom outline 82, while still maintaining the sealing relationship between the seal and the patient's face. The vent tube is allowed to deform the mask body without disturbing the sealing relationship by redistributing the external loads on the mask body. As applied here, the term "laterally" means movement or rotation of the vent tube either up or down as indicated by arrow 28 in FIG. 1, or sideways as indicated by directional arrow 84 in FIG. 8, or in a direction that is a combination of the two. The amount of deformation or flex in the mask body can be determined by measuring the maximum amount of bending of the mask body and lateral movement of the vent tube before the sealing relationship is broken. Without any lateral stresses, the connection of the vent tube with the mask body can be viewed as being oriented or centered on center axis 88, which is roughly perpendicular to the plane 30 of the patient's face. When the mask body flexes due to lateral stresses on the vent tube, the connection of the vent tube with the mask body will be centered on a new axis, phantom axis 90.

The amount of relative movement of the mask body can be measured by determining the angle between the unstressed axis 88 and the axis 90 of the flexed mask body 82, as indicated by angle 92. The more flexible the material and structure of the mask body 14, the greater the angle through which the mask body can be rotated without breaking the seal. Preferably, the mask body has sufficient flexibility that the vent tube can be rotated at least 30 degrees without breaking the sealing relationship between the seal and the patient's face. Most preferably, the vent tube can be rotated at least 60 degrees without breaking the sealing relationship between the seal and the patient's face.

Figure 9:
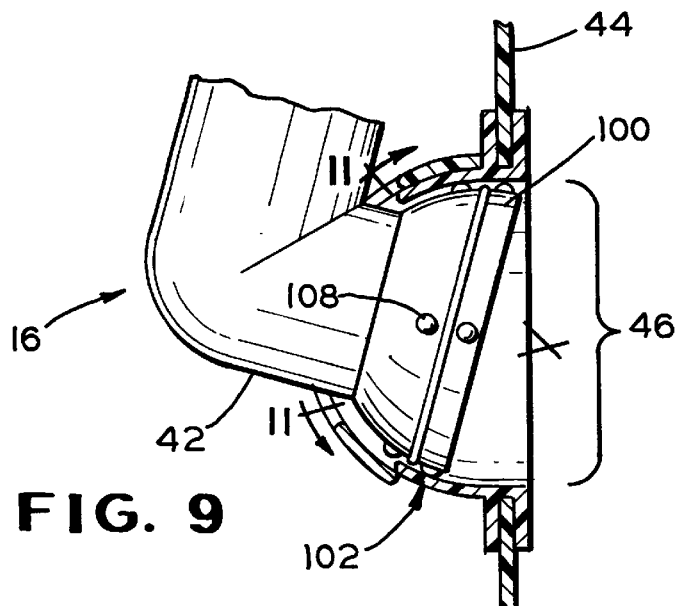
FIG. 9 is a schematic cross-sectional view in elevation showing the ball and socket connection between the vent tube and the mask body.
Figure 10:
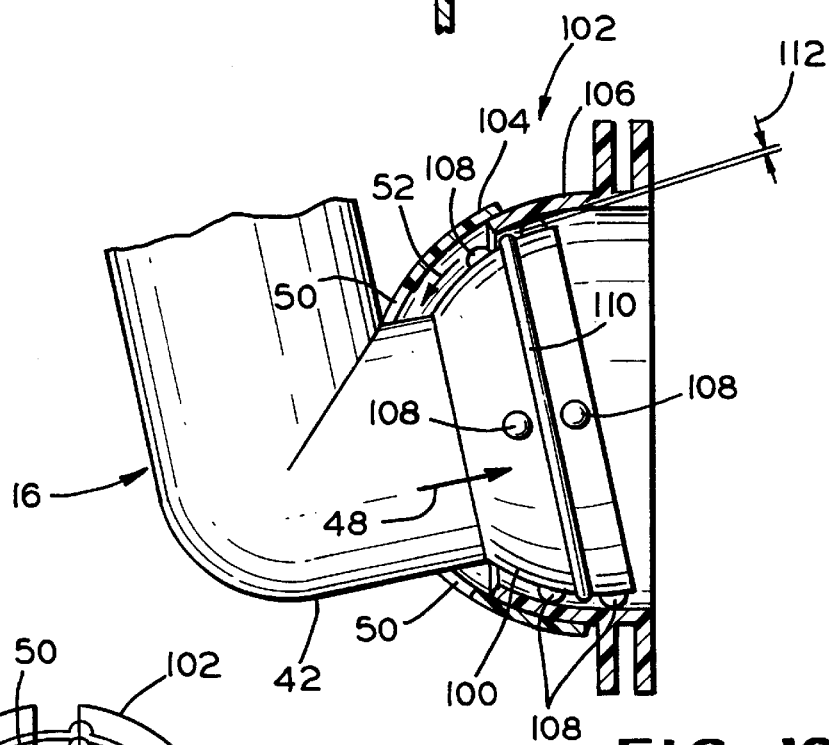
FIG. 10 is view similar to FIG. 9, but with the vent tube rotated to a different angle.
Figure 11:
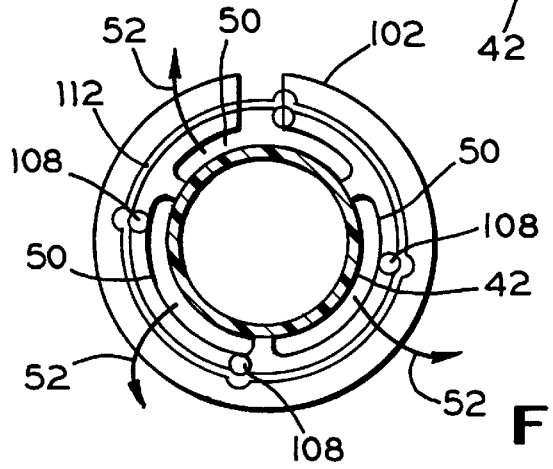
FIG. 11 is a cross-sectional view through the exit air vents, taken along lines 11—11 in FIG. 9.

As shown in FIGS. 9–11, the ball and socket connection 46 is comprised of an inner shell 100 and outer shell 102 which together define the path 52 for exhaled air. The outer shell 102 is comprised of two telescoping shell surfaces, shell surface 104 which is attached to the body leg of the vent tube, and shell surface 106 which is attached to the inlet end 44 of the mask body 14. The shell surfaces 104, 106 have similar curvatures so that they can swivel in any direction with respect to each other.

The inner shell 100 is mounted on or molded into the body leg 42 of the vent tube 16. The inner shell is provided with circumferentially arranged nubs or protuberances 108 which slide in contact with the shell surface 106 and act as spacers to maintain the proper spacing between the inner shell 100 and the outer shell 102. Since the protuberances are small in width, they do not obstruct the flow of exhaled air along the exhaled air path 52. Any suitable spacers can be used to keep the inner and outer shells at the proper separation. However, the inner shell is provided with an annular rim or ridge 110 to control the flow of exhaled air along the exit air path. The annular ridge has a diameter just slightly smaller than the inner diameter of the shell surface 106 so that a gap 112 is formed between them. The gap is preferably within the range of from about 0.011 to about 0.022 in.$^2$ (0.071 to 0.14 cm$^2$), and most preferably the gap is 0.018 in.$^2$ (0.116 cm$^2$). It can be seen that the path 52 for exhaled air includes traveling through the gap 112 and then through the exit air vents 50, where the exhaled air is directed away from the patient's face, as indicated by the arrows 52 in FIG. 11. The exhaled air is quite diffused by being able to exit through the relatively wide air exits 50, as shown in FIG. 11. Therefore the face mask of the invention provides little in the way of forceful or noisy pulses of exhaled air.

The principle and mode of operation of this invention have been described in its preferred embodiment. However, it should be noted that this invention may be practiced otherwise than as specifically illustrated and described without departing from its scope.

What is claimed is:

1. A mask for directing air to the facial area of a patient comprising: a mask body in the form of a conduit, a seal connected to an outlet end of said mask body for contacting such patient's face in a sealing relationship, said seal being soft and pliable for patient comfort, and a vent tube connected to an inlet end of said mask body to supply air to said mask body, wherein said mask body is relatively flexible compared with said vent tube so that lateral stresses on said mask body are initially accommodated by distortion of said mask body rather than on breaking the sealing relationship between the seal and such patient's face, and a frame mounted for movement along said mask body, said frame having an opening through which said mask body extends, where movement of said frame toward said outlet end of said mask body and into contact with said seal causes said frame to press said seal against such patient's face.

2. A mask for directing air to the facial area of a patient comprising: a mask body in the form of a conduit, a seal connected to an outlet end of said mask body for contacting such patient's face in a sealing relationship, said seal being soft and pliable for patient comfort, and a vent tube connected to an inlet end of said mask body to supply air to said mask body, wherein said mask body is relatively flexible compared with said vent tube so that lateral stresses on said mask body are initially accommodated by distortion of said mask body rather than on breaking the sealing relationship between the seal and such patient's face, and wherein said seal includes a mask body flange extending radially outwardly from outlet end of said mask body, thereby forming an outer circumferential edge, and a soft and flexible patient face flange connected to said outer circumferential edge and extending radially inwardly from said outer circumferential edge.

3. A mask for directing air to the facial area of a patient comprising: a mask body in the form of a conduit; a seal connected to an outlet end of said mask body for contacting such patient's face in a sealing relationship, said seal being soft and pliable for patient comfort; and a frame mounted for movement along said mask body, said frame having an opening through which said mask body extends, where movement of said frame toward said outlet end of said mask body and into contact with said seal causes said frame to press said seal against such patient's face.

4. The mask of claim 3 wherein said frame is relatively hard compared to said seal.

5. The mask of claim 4 including adjustable head gear connected to said frame to be extendible around such patient's head, wherein said headgear is adjustable to allow said frame to be forced toward said outlet end of said mask body, thereby urging said seal to contact such patient's face in a sealing relationship.

6. (Amended) The mask of claim 3 wherein said seal includes a mask body flange extending radially outwardly from said outlet end of said mask body, thereby forming an outer circumferential edge, and a soft and flexible patient face flange connected to said outer circumferential edge and extending radially inwardly from said outer circumferential edge.

7. The mask of claim 3 wherein said mask body and said seal are integrally molded together.

8. The mask of claim 3 wherein said frame opening is sufficiently large so that said mask body can be angled relative to said frame, thereby enabling said mask body to move independently of said frame.

9. The mask of claim 3 in which, prior to being pressed against such patient's face by said frame, said seal is contoured to conform to a predetermined facial shape.

10. The mask of claim 9 wherein said frame is contoured to conform to the shape of said seal.

11. A mask for directing air to the facial area of a patient comprising: a mask body in the form of a conduit; a seal connected to an outlet end of said mask body for contacting such patient's face in a sealing relationship, said seal being soft and pliable for patient comfort; and a frame mounted for movement along said mask body, said frame having an opening through which said mask body extends; where movement of said frame toward said outlet end of said mask body and into contact with said seal causes said frame to press said seal against such patient's face; said frame including a nose bridge portion, an upper jaw portion, and two lateral portions, and wherein said two lateral portions of said frame are contoured to conform to the shape of said seal so that gentle contact between said frame and said seal causes said two lateral portions of said frame to touch said seal; and wherein said nose bridge and said upper jaw portions of said frame are contoured out of conformance with the shape of said seal so that gentle contact between said frame and said seal does not cause said nose bridge and said upper jaw portions of said frame to touch said seal.

12. The mask of claim 11 wherein said nose bridge and said upper jaw portions of said frame are spaced sufficiently close to said seal when said frame and said seal are subjected to gentle contact that forceful contact between said frame and said seal causes said nose bridge and said upper jaw portions of said frame to touch said seal.

13. The mask of claim 11 in which, prior to being pressed against such patient's face by said frame, said seal is contoured to conform to a predetermined facial shape.

14. The mask of claim 11 wherein said frame is relatively hard compared to said seal.

15. The mask of claim 11 including adjustable head gear connected to said frame to be extendible around such patient's head, and wherein said headgear is adjustable to allow said frame to be forced toward said outlet end of said mask body, thereby urging said seal to contact such patient's face in a sealing relationship.

16. The mask of claim 11 wherein said seal includes a mask body flange extending radially outwardly from said outlet end of the mask body, thereby forming an outer circumferential edge, and a soft and flexible patient face flange connected to said outer circumferential edge and extending radially inwardly from said outer circumferential edge.

17. The mask of claim 11 wherein said frame opening is sufficiently large so that said mask body can be angled relative to said frame, thereby enabling said mask body to move independently of said frame.

18. A mask for directing air to the facial area of a patient comprising: a mask body in the form of a conduit; a seal connected to an outlet end of said mask body for contacting such patient's face in a sealing relationship, said seal being soft and pliable for patient comfort; a frame mounted for movement along said mask body, said frame having an opening through which said mask body extends, where movement of said frame toward the outlet end of said mask body and into contact with said seal causes said frame to press said seal against said patient's face; and an adjustable spacer positioned between said frame and said seal, said spacer being adjustable to vary the contact between said frame and said seal, thereby enabling said frame to selectively press against said seal so that the shape of said seal can be modified to conform to the shape of such patient's face.

19. The mask of claim 18 wherein said spacer is a bendable elongated member having two ends connected to said frame, said elongated member having a relatively flexible central portion bowed out toward said seal to vary contact between said frame and said seal, and wherein at least one of said ends of the spacer is relatively stiff for engagement with said frame.

20. The mask of claim 19 wherein at least one of said spacer ends is moveable with respect to said frame to vary the contact between said frame and said seal.

21. The mask of claim 19 wherein said at least one relatively stiff end of said spacer has a series of projections which can be selectively engaged with an opening in said frame to vary the contact between said frame and said seal.

22. The mask of claim 18 wherein one of said spacer ends is fixed to said frame and the other of said spacer ends is adjustable with respect to said frame to vary the contact between said frame and said seal.

23. The mask of claim 18 including adjustable head gear connected to said frame to be extendible around such patient's head, and wherein said headgear is adjustable to allow said frame to be forced toward said outlet end of said mask body, thereby urging said seal to contact such patient's face in a sealing relationship.

24. The mask of claim 23 wherein said frame opening is sufficiently large so that said mask body can be angled relative to said frame, thereby enabling said mask body to move independently of said frame.

25. The mask of claim 24 wherein said frame is contoured to conform to the shape of said seal.

26. A mask for directing air to the facial area of a patient comprising: a mask body in the form of a conduit; a seal connected to an outlet end of said mask body for contacting such patient's face in a sealing relationship, a vent tube connected to an inlet end of said mask body to supply air to said mask body and to act as an exit for air exhaled by such patient, said vent tube including a ball and socket connection to said mask body and an exit air vent located to direct exhaled air away from such patient's face; and wherein said ball and socket connection includes an inner shell and an outer shell, and spacers separating said inner and outer shells.

27. The mask of claim 26 wherein said spacers are protuberances on said inner shell.

28. The mask of claim 26 wherein a space between said separated inner and outer shells define an exit path for exhaled air to move to said exit air vent.

29. The mask of claim 28 wherein said exit path for exhaled air to move to said exit air vent is different from the path of air supplied to said mask.

30. The mask of claim 28 wherein the flow of exhaled air through the exit path is controlled by an annular ridge on the inner shell.

31. A mask for directing air to the facial area of a patient comprising: a mask body in the form of a conduit; a seal connected to an outlet end of said mask body for contacting such patient's face in a sealing relationship, a vent tube connected to an inlet end of said mask body to supply air to said mask body and to act as an exit for air exhaled by such patient, where said vent tube includes a ball and socket connection to said mask body and an exit air vent located to direct exhaled air away from such patient's face, wherein said ball and socket connection includes an inner shell and an outer shell, and spacers separating said inner and outer shells, wherein said spacers are protuberances on said inner shell, wherein a space between said separated inner and outer shells define an exit path for exhaled air to move to said exit air vent, wherein the exit path for exhaled air to move to the exit air vent is different from the path of air supplied to said mask, and wherein the flow of exhaled air through the exit air path is controlled by an annular ridge on said inner shell.

* * * * *